United States Patent
Wallnewitz et al.

(10) Patent No.: US 10,420,910 B2
(45) Date of Patent: Sep. 24, 2019

(54) BREATHING MASK WITH EMERGENCY BREATHING VALVE

(71) Applicant: Drägerwerk AG & Co. KGaA, Lübeck (DE)

(72) Inventors: Oliver Wallnewitz, Lübeck (DE); Helena Kaszás, Gross Grönau (DE); Krisztina Soltész, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 975 days.

(21) Appl. No.: 14/893,257

(22) PCT Filed: Mar. 8, 2014

(86) PCT No.: PCT/EP2014/000591
§ 371 (c)(1),
(2) Date: Nov. 23, 2015

(87) PCT Pub. No.: WO2014/187511
PCT Pub. Date: Nov. 27, 2014

(65) Prior Publication Data
US 2016/0184548 A1 Jun. 30, 2016

(30) Foreign Application Priority Data

May 24, 2013 (EP) ..................................... 13169183

(51) Int. Cl.
*A61M 16/20* (2006.01)
*A61M 16/06* (2006.01)
*A61M 16/00* (2006.01)

(52) U.S. Cl.
CPC ...... *A61M 16/208* (2013.01); *A61M 16/0078* (2013.01); *A61M 16/06* (2013.01)

(58) Field of Classification Search
CPC .............. A61M 16/208; A61M 16/209; A61M 16/0078; A61M 16/06; A61M 16/206;
(Continued)

(56) References Cited

U.S. PATENT DOCUMENTS 3,097,642 A * 7/1963 Russell ................. A61M 16/06
128/205.17
3,643,686 A * 2/1972 Koegel .................. A61B 5/097
128/205.24
(Continued)

FOREIGN PATENT DOCUMENTS

CN 2629755 Y 8/2004
CN 1548189 A 11/2004
(Continued)

*Primary Examiner* — Jan Christopher L Merene
*Assistant Examiner* — Brian M. Booker
(74) *Attorney, Agent, or Firm* — McGlew and Tuttle, P.C.

(57) ABSTRACT

A breathing mask has a mask body surrounding a cavity that is open towards one side and is intended for coming into contact with a human face around the mouth and/or nose. A valve arrangement is provided in the mask body with an inspiration valve, for controlling the flow of gas from a port for a breathing gas feed device for providing a breathing gas into the cavity, and an exhalation valve for controlling the flow of gas from the cavity into the surrounding atmosphere. An emergency breathing valve, controlling gas flow from the atmosphere surrounding the breathing mask into the cavity, has a pressure threshold, to allow gas flow, that is lower than an inhalation valve pressure threshold. The pressure thresholds at which the respective inhalation valve and the emergency breathing valve open are coordinated by the closing element being designed as a separate component of the valve arrangement.

17 Claims, 5 Drawing Sheets

(58) Field of Classification Search
CPC ............. A61M 16/10; A61M 5/1723; A61M 16/0468; A61M 16/0488; A62B 23/06; A62B 7/10; Y10T 137/778; Y10T 137/88022; Y10T 137/8803; Y10T 137/88038; Y10T 137/88062; A41D 13/11; A61B 5/085; A61B 5/091; F16K 11/10; F16K 1/44; F16K 1/443

See application file for complete search history.

(56) References Cited

U.S. PATENT DOCUMENTS

| | | | | |
|---|---|---|---|---|
| 4,071,025 | A * | 1/1978 | Kohnke | A61M 16/208 128/205.13 |
| 4,164,942 | A | 8/1979 | Beard et al. | |
| 4,691,623 | A * | 9/1987 | Mizusawa | B60H 1/249 137/512.15 |
| 4,807,614 | A * | 2/1989 | van der Smissen | A62B 17/04 128/201.23 |
| 5,724,962 | A * | 3/1998 | Vidgren | A61M 16/208 128/200.14 |
| 6,631,721 | B1 * | 10/2003 | Salter | A61M 11/06 128/203.21 |
| 7,044,164 | B2 * | 5/2006 | Carlson | B60H 1/249 137/315.33 |
| 7,066,174 | B1 * | 6/2006 | Smith | A61M 16/208 128/204.18 |
| 7,185,652 | B2 * | 3/2007 | Gunaratnam | A61M 16/06 128/202.27 |
| 7,360,538 | B2 * | 4/2008 | Flynn | A61M 16/06 128/204.28 |
| 7,726,314 | B1 * | 6/2010 | Ming | A61M 16/06 128/202.27 |
| 7,753,073 | B2 * | 7/2010 | Owczarczak | A61M 16/08 128/204.18 |
| 8,020,556 | B2 * | 9/2011 | Hayek | A61M 16/0096 128/204.18 |
| 8,342,179 | B2 * | 1/2013 | Hacke | A61M 16/06 128/206.12 |
| 8,360,104 | B2 * | 1/2013 | Shereyk | B60H 1/249 137/852 |
| 8,464,715 | B2 * | 6/2013 | Flynn, Sr. | A61M 16/0078 128/205.24 |
| 8,646,449 | B2 * | 2/2014 | Bowsher | A61M 16/06 128/201.28 |
| 8,757,156 | B2 * | 6/2014 | Martin | A62B 23/025 128/205.27 |
| 8,783,252 | B2 * | 7/2014 | Pierro | A61B 5/08 128/205.25 |
| 8,814,806 | B2 * | 8/2014 | Kullik | A61B 5/0876 128/205.23 |
| 9,913,953 | B2 * | 3/2018 | Moody | A61M 16/00 |
| 10,088,065 | B2 * | 10/2018 | Olejak | F16K 15/038 |
| 2001/0035188 | A1 | 11/2001 | Gleason et al. | |
| 2003/0024533 | A1 * | 2/2003 | Sniadach | A61M 16/06 128/205.25 |
| 2003/0062040 | A1 * | 4/2003 | Lurie | A61M 16/20 128/203.11 |
| 2004/0211428 | A1 * | 10/2004 | Jones, Jr. | A61M 16/06 128/206.27 |
| 2005/0098183 | A1 * | 5/2005 | Nash | A61M 16/06 128/206.21 |
| 2005/0145247 | A1 | 7/2005 | Nashed | |
| 2006/0249158 | A1 | 11/2006 | Dhuper et al. | |
| 2007/0267019 | A1 * | 11/2007 | Lugtigheid | A61M 16/208 128/205.13 |
| 2007/0277829 | A1 * | 12/2007 | Casewell | A62B 18/02 128/206.24 |
| 2008/0053446 | A1 * | 3/2008 | Sleeper | A61M 16/06 128/205.25 |
| 2008/0142013 | A1 * | 6/2008 | Hallett | A61M 16/06 128/205.24 |
| 2009/0270752 | A1 * | 10/2009 | Coifman | A61B 5/087 600/538 |
| 2010/0199991 | A1 * | 8/2010 | Koledin | A61M 16/08 128/205.12 |
| 2010/0249584 | A1 * | 9/2010 | Albertelli | A61B 5/0813 600/431 |
| 2011/0083670 | A1 * | 4/2011 | Walacavage | A61M 16/06 128/205.12 |
| 2011/0120473 | A1 * | 5/2011 | Piper | A61M 16/208 128/207.16 |
| 2011/0155136 | A1 * | 6/2011 | Lee | A61M 16/06 128/205.24 |
| 2012/0000472 | A1 * | 1/2012 | Martucci | A61M 16/0488 128/861 |
| 2012/0012116 | A1 * | 1/2012 | Bare | A61M 16/0468 128/207.16 |
| 2012/0103338 | A1 * | 5/2012 | Chan | A61M 16/06 128/205.24 |
| 2012/0111330 | A1 * | 5/2012 | Gartner | A61M 16/06 128/205.23 |
| 2012/0289851 | A1 * | 11/2012 | Varga | A61B 5/0836 600/532 |
| 2014/0096768 | A1 * | 4/2014 | Lee | A61M 16/06 128/202.27 |
| 2014/0128676 | A1 * | 5/2014 | Law | A61B 1/00 600/114 |
| 2014/0150801 | A1 * | 6/2014 | Rusher | A63B 23/18 128/207.16 |
| 2014/0196726 | A1 * | 7/2014 | Mallek | A61M 16/0816 128/861 |
| 2014/0283837 | A1 * | 9/2014 | Turrisi | A61M 16/0078 128/205.13 |

FOREIGN PATENT DOCUMENTS

| | | |
|---|---|---|
| CN | 102319491 A | 1/2012 |
| EP | 1 854 494 B1 | 6/2012 |
| GB | 1 553 437 A | 9/1979 |
| KR | 20 2009 0008082 U | 8/2009 |
| WO | 01/78838 A2 | 10/2001 |

* cited by examiner

BREATHING MASK WITH EMERGENCY BREATHING VALVE

CROSS REFERENCE TO RELATED APPLICATIONS

This application is a United States National Phase Application of International Application PCT/EP2014/000591 filed Mar. 8, 2014 and claims the benefit of priority under 35 U.S.C. § 119 of European Patent Application 13 169 183.4 filed May 24, 2013 the entire contents of which are incorporated herein by reference.

FIELD OF THE INVENTION

The present invention pertains to a breathing mask with a mask body, which surrounds a cavity that is open towards one side and which is intended for being in contact with a human face around the mouth and/or nose thereof, wherein the mouth and/or nose may be arranged in the cavity, with a feed port for connecting a breathing gas feed device for feeding gas into the cavity, with a valve arrangement, which has an exhalation valve for controlling the flow of gas from the cavity into the atmosphere surround the breathing mask and an emergency breathing valve for controlling the flow of gas from the atmosphere surrounding the breathing mask into the cavity, wherein the exhalation valve has a closing body for closing an exhalation valve opening, and the exhalation valve is adapted such that it opens when the pressure in the cavity is above the pressure of the atmosphere surrounding the breathing mask by a preset value, wherein the emergency breathing valve is adapted such that it opens when the pressure in the cavity is below the pressure of the atmosphere surrounding the breathing mask by a preset value, wherein the emergency breathing valve has a diaphragm element, which is provided with a diaphragm opening, which forms a gas connection between the cavity and the atmosphere surrounding the breathing mask, wherein the emergency breathing valve has a closing element with a closing surface, which said closing element is designed to have such a flexibility that it is deformable between an open position, in which the closing surface is located at a spaced location from the diaphragm element, so that a flow of gas through the opening is allowed, and a closed position, in which the closing surface is in contact with the diaphragm element, so that the closing element closes the diaphragm opening towards the atmosphere surrounding the breathing mask and gas is prevented from flowing through the diaphragm opening. Furthermore, the present invention pertains to a ventilation system with a breathing mask.

BACKGROUND OF THE INVENTION

Such breathing masks are used especially to supply a patient with oxygen, the feed port being connected to a breathing gas supply and especially to an oxygen supply, which has an inhalation valve, which controls a flow of breathing gas into the cavity and which is designed such that it will open when the pressure in the cavity is below the pressure prevailing in the breathing gas supply by a preset value. A gas or oxygen bag, which is, in turn, connected to the oxygen supply, is usually provided in this case in the breathing gas supply. The oxygen bag is thus used as a buffer, and it is not necessary for the oxygen supply to provide such a large volume flow as this would be necessary during the inhalation phase, when the patient is breathing in. It is rather sufficient for the oxygen supply to provide a volume flow that corresponds to the time average of the patient's oxygen intake.

In addition, an exhalation valve is provided in the breathing mask, and this valve opens when a pressure that is higher than the ambient pressure builds up in the interior of the cavity during the exhalation phase. The exhalation valve is consequently designed such that it only allows a flow from the cavity to the outside, i.e., a higher pressure must prevail in the cavity than in the surrounding area.

Such breathing masks, which have only an exhalation valve in conjunction with an inhalation valve in the breathing gas supply, have the drawback that there is a risk that the patient will not be sufficiently supplied with breathing gas when the volume flow of the breathing gas supply is lower than the patient's demand or fails to materialize altogether. It may happen in such a situation that the volume present in the oxygen bag is consumed by the patient and the patient will then no longer be supplied with more breathing gas.

To avoid this problem, it is known from EP 1 854 494 B1 that an emergency breathing valve is also provided besides the inhalation valve and the exhalation valve. The emergency breathing valve provides for a connection between the cavity and the area surrounding the breathing mask and is designed such that it only opens when a pressure that is lower than the pressure at which the inhalation valve would already open prevails in the cavity of the breathing mask. This causes the emergency breathing valve to open only when the patient is no longer receiving breathing gas from the breathing gas supply during the inhalation phase and a lower pressure is therefore building up in the cavity than is necessary to open the inhalation valve.

The valve body, which closes or opens the inhalation valve, the valve body, which closes or opens the exhalation valve, and the valve body of the emergency breathing valve are made in one piece from a flat, flexible material in the design described on EP 1 854 494 B1, on which the present invention is based. However, this is associated with the drawback that the pressure thresholds at which the inhalation valve and the emergency breathing valve open and which must be coordinated with one another can be set with highly insufficient precision only.

SUMMARY OF THE INVENTION

Therefore, based on the state of the art, an object of the present invention is to provide a breathing mask in which the respective pressure thresholds at which the inhalation valve and the emergency breathing valve open can be coordinated with one another with high accuracy.

This object is accomplished according to the present invention by the closing element of the emergency breathing valve being designed as a separate component of the valve arrangement.

Due to the closing element of the emergency breathing valve being designed as a separate component, the material and the elastic properties of said component, which are associated with the material, as well as the dimensions of said component can be selected entirely independently from those of the closing element of the exhalation valve. This leads to a great freedom and hence also to the possibility of accurately setting the threshold at which the emergency breathing valve opens.

The closing element preferably has a first connection element, wherein the diaphragm element is provided with a second connection element for meshing with the first connection element. In particular, the first connection element may be surrounded by the closing surface, and the second connection element is arranged within the diaphragm opening and has an arm extending radially towards the edge of the diaphragm opening. One of the connection elements may be designed here as a pin extending away from the diaphragm opening, while the other of the connection elements is designed as a mounting opening for meshing with the pin. Such a design allows a simply assembly of the closing element. In addition, the closing element can be easily replaced. It is possible in this connection, on the one hand, that the pin is formed on the closing element and the mounting opening in a mounting bush, which is provided on at least one arm extending from the edge of the diaphragm opening. Conversely, the pin may, however, also be provided on the at least one arm, while the mounting opening is formed in the closing element.

In another preferred embodiment, the diaphragm opening is designed as a separate component, which is fastened to the mask body on the side facing away from the cavity, the closing body of the exhalation valve being held on the side pointing away from the cavity between the diaphragm element and the mask body. Such a design makes possible a very simple mounting of the elements of the emergency breathing valve and of the exhalation valve on the mask body, because the diaphragm element fixes at the same time the closing body of the exhalation valve during its mounting. If, in addition, the diaphragm element is also designed as a separate component, the elements that provide the function of the emergency breathing valve are completely separated from those that form the exhalation valve.

Furthermore, it is preferred in this connection if the exhalation valve has two separate exhalation valve openings adjoining the diaphragm element, wherein the closing body is made in one piece and has two flaps extending away from the diaphragm element. This makes possible, on the one hand, the simple mounting of the elements of the emergency breathing valve and of the exhalation valve, and it is ensured, on the other hand, that the opening cross section of the exhalation valve is sufficiently large, on the one hand, but it can, on the other hand, be reliably closed by the closing element, because the surfaces of the flaps of the closing element can be selected to be comparatively small, but the opening will nevertheless have a large cross-sectional area as a sum.

The closing body of the exhalation valve is preferably designed such that it also has a central opening, through which the diaphragm element partially extends and above which the diaphragm opening is arranged, so that the closing body can be reliably clamped on the mask body as a result.

Finally, it is preferable to design the closing body as a symmetrical body, in which case the exhalation valve openings and the flaps of the closing body are arranged on opposite sides of the diaphragm element.

Finally, the mask body of the breathing mask may be designed in another preferred embodiment such that it has a main section made of a flexible material, within which a valve section made of a hard plastic is provided, which receives the valve arrangement. The main section is formed from a flexible material, which readily fits the shape of the mouth and nose area of the patient, while the valve section facilitates the mounting due to its rigidity and makes possible a reliable sealing especially of the exhalation valve.

According to a second aspect of the present invention, a ventilation system with an above-described breathing mask is provided, wherein the feed port is connected to a breathing gas feed device.

In particular, the breathing gas feed device may have a gas bag, which is provided with a connection piece, which is connected to the feed port, wherein the connection piece has an inhalation valve to control the flow of gas from the connection piece into the cavity, and wherein the inhalation valve is adapted such that it opens when the pressure in the cavity is lower than the pressure in the connection piece by a preset value. Furthermore, the connection piece may have a port for a breathing gas supply line.

The present invention will be explained below on the basis of a drawing showing only a preferred exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
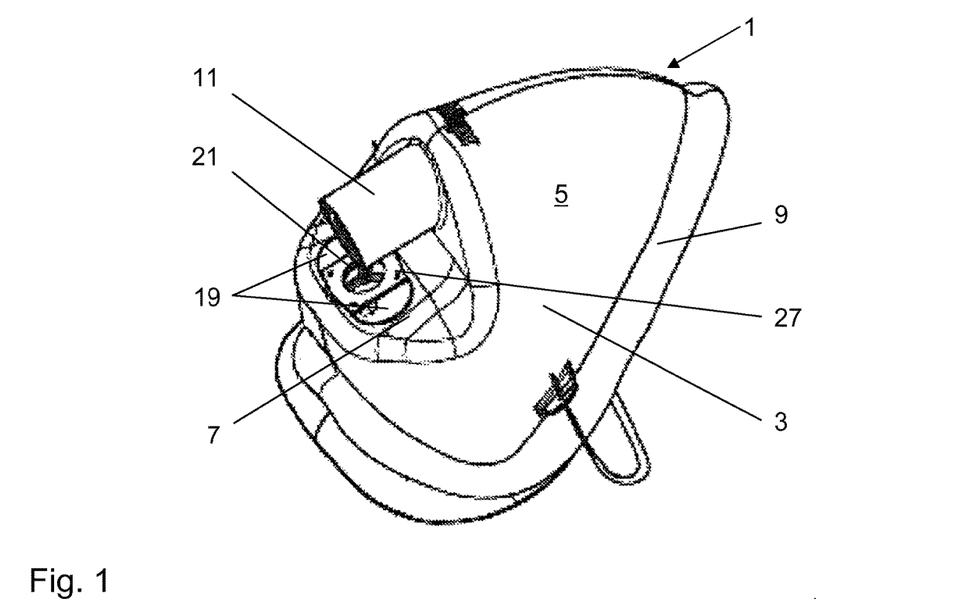
FIG. 1 is a perspective view of an exemplary embodiment of a breathing mask according to the present invention.
Figure 3:
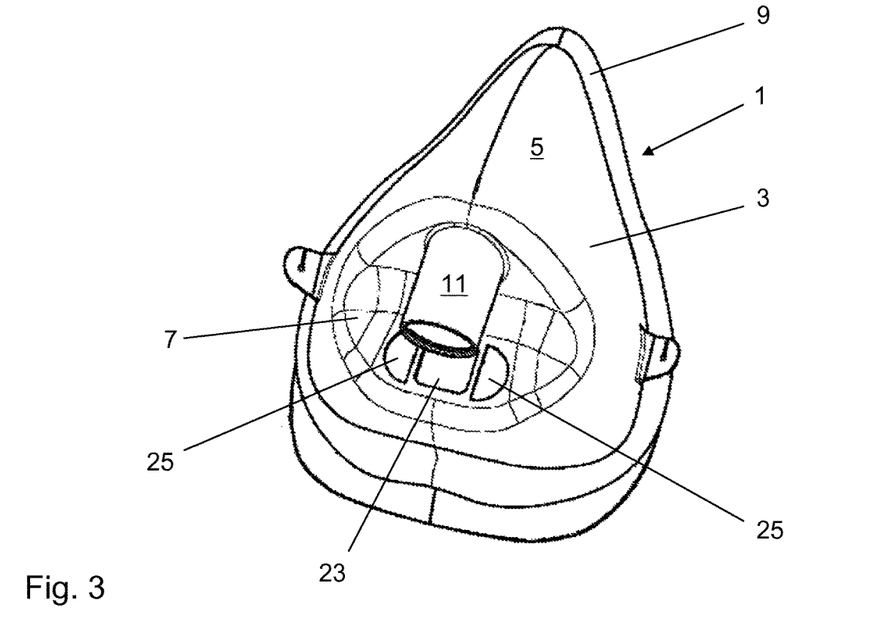
FIG. 3 is a perspective front view of the exemplary embodiment of the breathing mask according to FIG. 1 without diaphragm element, closing element and closing body.

As is seen especially in FIGS. 1 and 3, the exemplary embodiment of a breathing mask 1 according to the present invention has a mask body 3, which has a two-part design, comprising a main section 5, which is formed from a flexible material, and a valve section 7, which is arranged therein and is formed from a hard plastic. The mask body 3 and especially the main section 5 are shaped such that a cavity is formed therein, which is adapted to be able to accommodate the mouth and nose of a patient, the flexible edge 9 of the main section 5 of the mask body 3 being in contact with the face of the patient, so that the cavity is sealed against the surrounding area.

Figure 2:
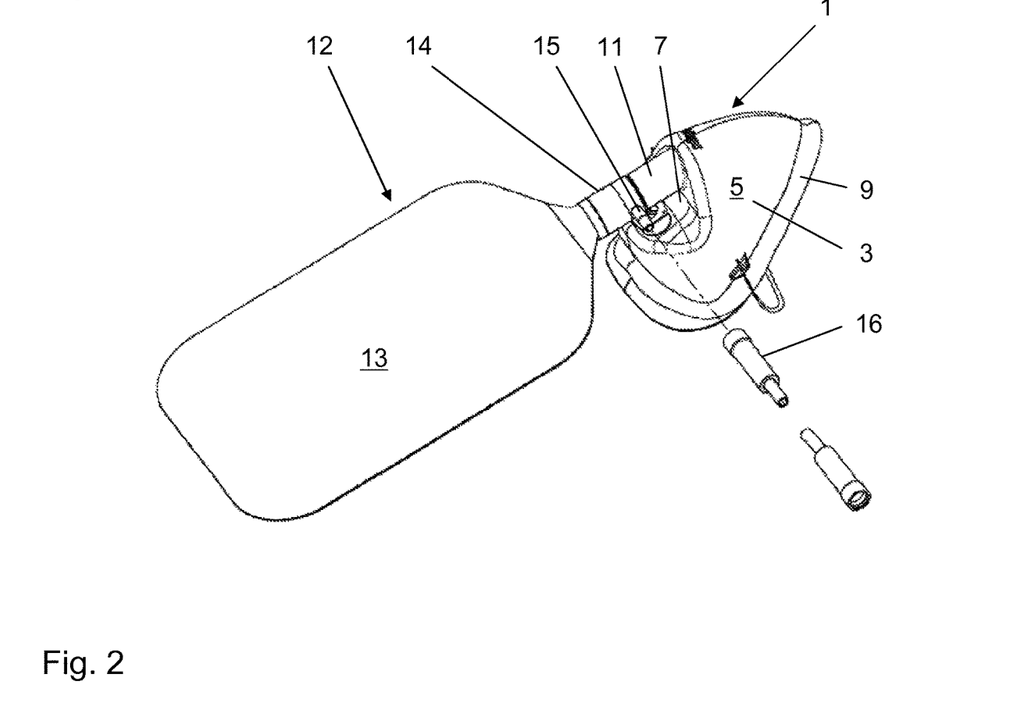
FIG. 2 is a perspective view of a combination of the exemplary embodiment according to FIG. 1 with a breathing gas feed device.
Figure 4:
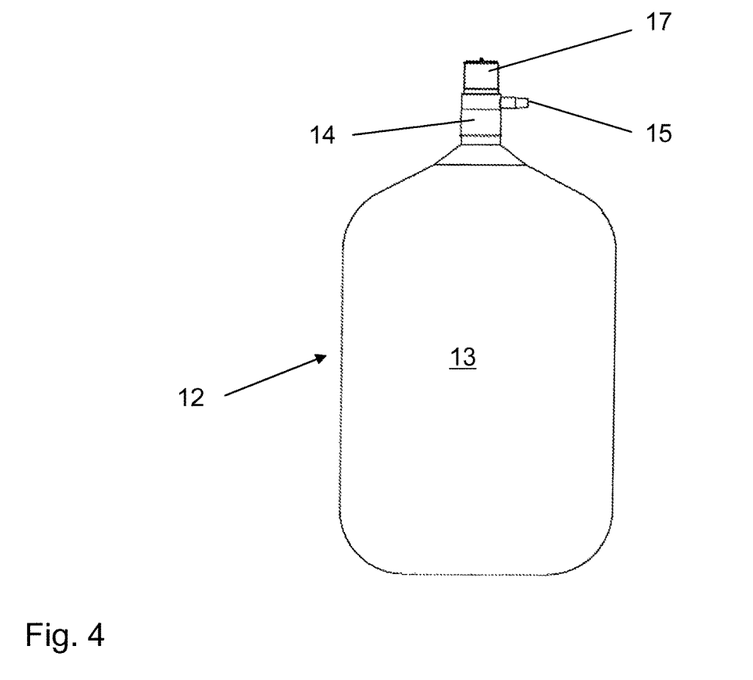
FIG. 4 is a side view of the oxygen bag of the breathing gas feed device separated from the breathing gas mask.

A feed port 11 is provided at the valve section 7, and the cavity of the breathing mask 1 can be connected via said feed port 11 to a breathing gas feed device 12, which latter has a gas or oxygen bag 13, which in turn has a connection piece 14. A port 15 for a breathing gas or oxygen supply 16, through which a constant volume flow of breathing gas enriched with oxygen is fed to the oxygen bag 13, is provided at the connection piece 14.

Furthermore, an inhalation valve 17 for controlling the flow of gas from the connection piece 14 into the cavity is provided in the connection piece 14 on the side of the port 15 facing away from the oxygen bag 13. The inhalation valve 17 is adapted such that it opens when the pressure in the cavity is below the pressure prevailing ion the connection piece 14 by a preset value. The inhalation valve 17 is thus normally closed and opens when the patient lowers the pressure in the cavity during inhalation.

An exhalation valve 19 as well as an emergency breathing valve 21 are arranged in the valve section 7 adjacent to the feed port 11, so that these valves 19, 21 form a valve arrangement, via which a gas connection to the cavity in the mask body 3 can be established. The design of the exhalation valve 19 as well as of the emergency breathing valve 21 are seen in detail in FIGS. 3, 5 and 6.

As is shown in FIG. 3, an emergency breathing valve opening 23 as well as two exhalation valve openings 25 arranged adjacent thereto at opposite edges are formed in the valve section 7 of the mask body 3. As can be seen in FIG. 1, a diaphragm element 27 is inserted into the emergency valve opening 23, the diaphragm element 27 being in contact with the mask body 3 on the side of said mask body 23 facing away from the cavity, and a closing body 31, which has a central opening 29 and is made in one piece, is clamped between the diaphragm element 27 and the mask body 3 or the valve section 7. This closing body 31 is part of the exhalation valve 19, and flaps 33, which are provided thereon and extend away from opposite edges of the diaphragm element 27, close the exhalation valve openings 25 by being in contact with the valve section 7 or the mask body 3 on the side pointing away from the cavity.

The central opening 29 in the closing body 31 is arranged, besides, such that it is arranged above the emergency breathing valve opening 23 and a central diaphragm opening 35 in the diaphragm element 27. The diaphragm opening 35 thus forms a gas connection between the cavity and the atmosphere surrounding the breathing mask 1.

Figure 5:
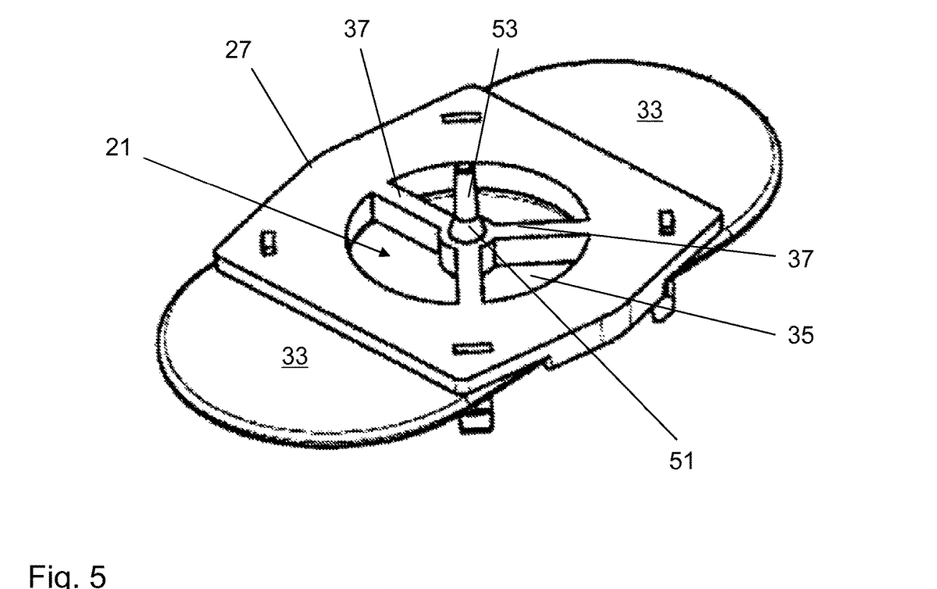
FIG. 5 is a perspective view of the diaphragm element together with the closing element and with the closing body of the exhalation valve according to the exemplary embodiment shown in FIGS. 1 and 3.
Figure 6:
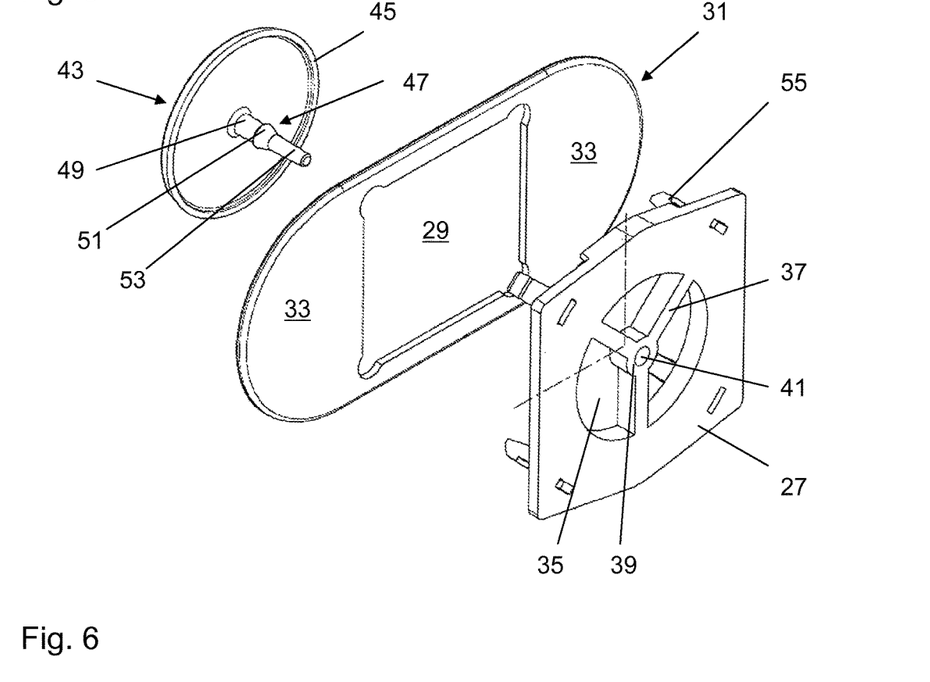
FIG. 6 is an exploded view of the diaphragm element, of the closing element and of the closing body of the exhalation valve.
Figure 7:
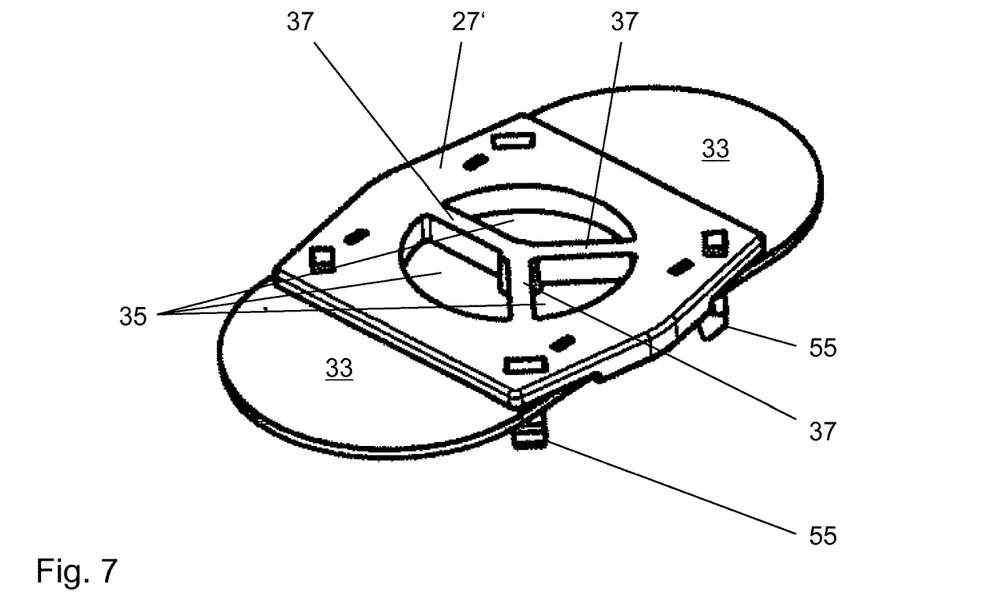
FIG. 7 is a perspective view of an alternative embodiment of the diaphragm element, of the closing element and of the closing body for the exemplary embodiment from FIGS. 1 and 3.
Figure 8:
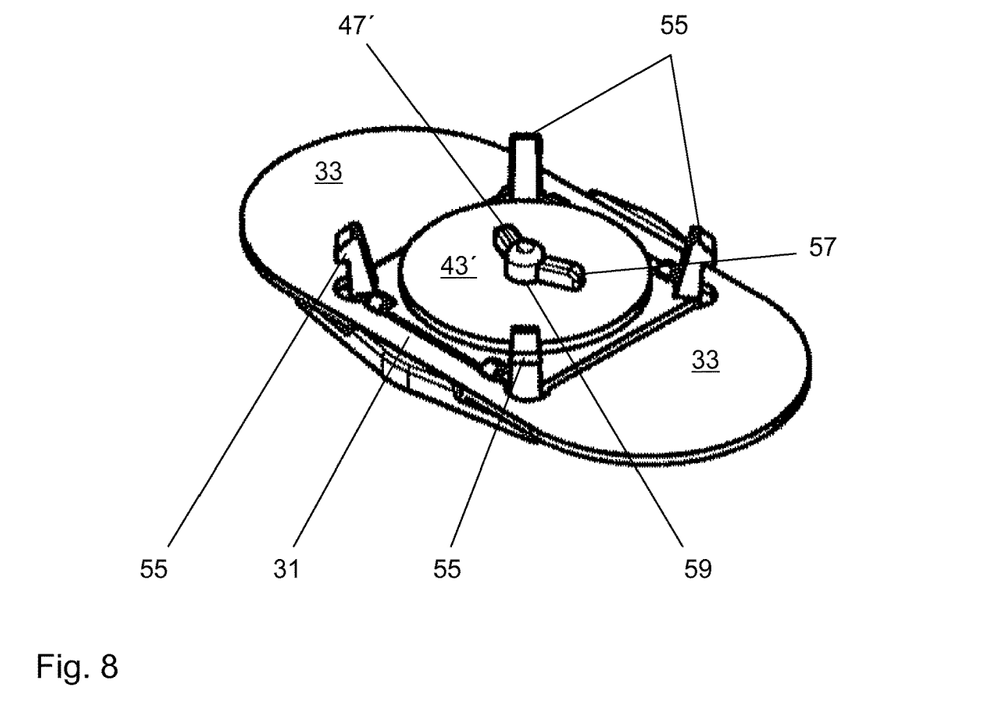
FIG. 8 is a second perspective view of the alternative embodiment from FIG. 7.
Figure 9:
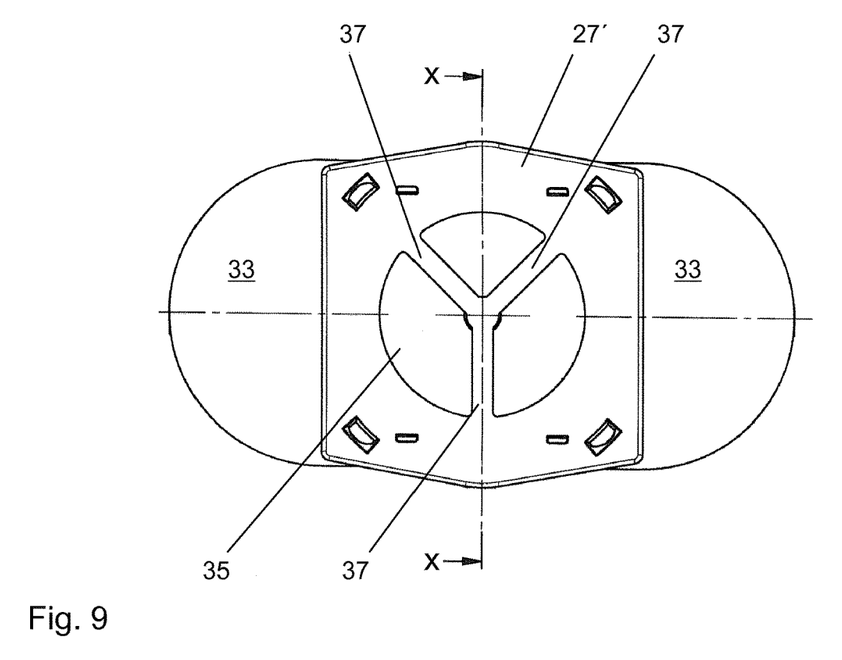
FIG. 9 is a top view of the alternative embodiment from FIG. 7.
Figure 10:
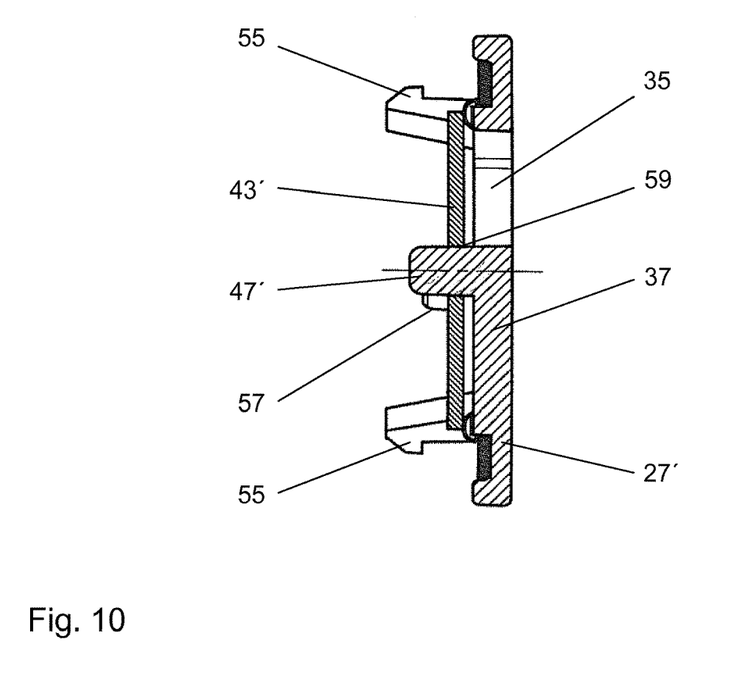
FIG. 10 is a sectional view taken along line X-X in FIG. 9.

Three arms 37, which extend radially away from the center of the diaphragm opening 35 and hold a central mounting bush 39, in which a mounting opening designed as a hole 41 is provided, are provided in the diaphragm opening 35. The closing element 43 of the emergency breathing valve, which has a circular shape and has a circular ring-shaped closing surface 45 pointing towards the diaphragm element 27 and is in contact therewith in the closed state, is provided on the side of the diaphragm element 27 pointing towards the cavity. A first connection element designed as a pin 47 extends at right angles to the diaphragm opening 35 and away from said opening as well as from the closing element 43 centrally on the closing element 43 and surrounded by the closing surface 45, said first connection element being intended for meshing with the second connection element in the diaphragm element 27, which said second connection element is designed as a hole 41 or mounting opening in the mounting sleeve 49. The pin 47 has a first section 49, which is adjoined by a cone 51, whose external diameter tapers away from the first section 49, wherein an undercut is formed between the cone 51 and the first section 49. The cone 51 is, in turn, adjoined by a second section 53 of the pin 47.

During mounting, the second section 53 as well as the cone 51 of the pin 47 are pulled through the hole 41 until the undercut between the cone 51 and the first section 49 comes into contact with the diaphragm element 27 on the side of said diaphragm element 27 facing away from the cavity and the closing element 43 is thus locked on the diaphragm element 27. The second section 53 of the pin 47 can be separated from the cone in this state, because the second section 53 acts here as a mounting aid only.

The arrangement comprising the closing body 31, the diaphragm element 27 and the closing element 43 is then fastened to the mask body 3 by means of the locking arms 55, which are provided on the diaphragm element 27 and mesh with the edge of the emergency breathing valve opening 23 in the valve section 7, and the diaphragm element 27 will then clamp the closing body 31 on the mask body 3 and the valve section 7.

The closing surface 45 of the closing element 43 designed as a separate component is normally in contact with the diaphragm element 27. However, when the pressure in the interior of the cavity is reduced relative to the surrounding atmosphere by a sufficiently high value, which is, moreover, higher than the value that is necessary to open the inhalation valve 17, the closing element 43 is bent away from the diaphragm element 27, so that the closing surface 45 is bent off from the diaphragm element 27 and a passage is created through the diaphragm opening 35 into the cavity and the patient will receive ambient air as breathing air in this manner.

The closing element 43 thus has such a flexible design that it can be deformed between an open position, in which the closing surface 45 is located at a spaced location from the diaphragm element 27, so that flow of gas through the diaphragm opening 35 is allowed, and a closed position, in which the closing surface 45 is in contact with the diaphragm element 27 on the side pointing towards the cavity in this exemplary embodiment and covers the diaphragm opening 35 towards the atmosphere surrounding the breathing mask 1, so that flow of gas through the diaphragm opening 35 is prevented from occurring. The closing surface 45 could, however, also come into contact with the mask body 3 in the closed position in case of different dimensions. The diaphragm element would then also be formed by the mask body in the sense of the present invention in such a case.

The emergency breathing valve 21 formed from the closing element 43 and the diaphragm element 27 is therefore adapted such that the pressure in the cavity that is necessary to allow flow of gas through the emergency breathing valve 21 is lower than the pressure in the cavity that is necessary to allow flow of gas through the feed port 11.

Due to the fact that the closing element 43 is designed as a separate component, it can be adapted very accurately insofar as the material and the dimensions are concerned in order to ensure that the condition that an opening takes place only when a pressure is present that is lower than the pressure that is needed to open the inhalation valve 17 will always be met. If this were not so, there would be a risk that the patient would receive breathing gas via the emergency breathing valve 21 even then, even though the breathing gas supply through the inhalation valve 17 is still available. As an alternative, the problem could, moreover, arise that the pressure that is necessary for opening the emergency breathing valve is too low and the patient must generate an excessively high vacuum, which thus represents a great effort, to be supplied with breathing gas when the breathing gas supply has failed.

In addition, a simple design of the exhalation valve 19, in which the closing body 31 having a one-piece design with the two flaps 33 is clamped and thus held by the diaphragm element 27, is obtained by the fact that the diaphragm element 27 and the emergency valve opening 23 are arranged between the two exhalation valve openings 25. The flaps 33 normally seal the exhalation valve openings 25. However, when the patient is exhaling and a pressure that is higher than the pressure of the atmosphere surrounding the breathing mask 1 by a preset value develops, the flaps 33 are bent away from the exhalation valve openings 25 and expose this, so that the exhaled air can escape from the cavity of the mask body 3.

The inhalation valve 17 normally opens during inhalation because of the vacuum generated by the patient in the cavity of the mask body 3, so that, for example, breathing gas enriched with oxygen will reach the patient either from the oxygen bag 13 or directly from the oxygen supply line 16. When the patient subsequently exhales, an overpressure builds up in the cavity relative to the surrounding area, so that the flaps 33 will subsequently be lifted off from the mask body 3 or the valve section 7.

In case the breathing gas provided in the oxygen supply line 16 and the oxygen bag 13 is not sufficient, a pressure that is lower than the pressure that is needed to open the inhalation valve 17 builds up in the cavity of the mask body 3. The emergency breathing valve 21 will then also open in this case, in such a way that the closing surface 45 is lifted off from the diaphragm element 27. It is thus ensured that the patient receives air for breathing in any case.

Moreover, it is ensured by the embodiment according to the present invention of the valve arrangement and especially of the combination of the emergency breathing valve 21 and the exhalation valve 19 that the aforementioned condition imposed on the opening behavior of the emergency breathing valve 21 and inhalation valve 17 is met, but simple mounting is nevertheless made possible.

FIGS. 7 through 10 show an alternative embodiment for the combination of the diaphragm element 27', closing element 43' and closing body 31 with flaps 33, which can likewise be used in the exemplary embodiment of the breathing mask 1 according to FIGS. 1 through 3.

This embodiment has a design similar to that shown in FIGS. 5 and 6, so that identical reference numbers are used for identical elements, and it likewise has a diaphragm element 27', which is provided with a diaphragm opening 35 and with locking arms 55 and with which a closing body 31 with flaps can be clamped on the mask body 3. Arms 37 extend into the diaphragm opening 35 from the edge thereof. A closing element 43', which is designed as a separate component here as well and which has a design similar to that of the closing element 43 from FIG. 6, is also formed on the arms 37 here.

This embodiment differs from that shown in FIGS. 5 and 6 in that the diaphragm element 27' has, on the arms 37 extending into the diaphragm opening 33, a pin 47', which extends away from the diaphragm element 27' at right angles to the diaphragm opening 35 and which extends to the closing element 43'. Further, the free end of the pin 47' is provided with a projection 57.

The closing element 43' is, in turn, provided, unlike in the embodiment according to FIGS. 5 and 6, with a mounting opening 59, through which the pin 47' with the projection 57 extends and fixes the closing element 43' on the diaphragm element 27' as a result.

Consequently, the first connection element is formed in this embodiment as a mounting opening 59 on the closing element 43', while the second connection element provided on the diaphragm element 27' is designed as a pin 47'.

However, the advantages explained in connection with the first embodiment are also achieved with this embodiment, because the closing body 43' is designed as a separate component of the valve arrangement here as well.

While specific embodiments of the invention have been shown and described in detail to illustrate the application of the principles of the invention, it will be understood that the invention may be embodied otherwise without departing from such principles.

The invention claimed is:

1. A breathing mask comprising: a mask body, which surrounds a cavity that is open towards one side and which is intended for coming into contact with a human face around the mouth and/or nose thereof, wherein the mouth and/or nose may be arranged in the cavity; a feed port for connecting a breathing gas feed device for feeding gas into the cavity; a valve arrangement comprising an exhalation valve for controlling the flow of gas from the cavity into atmosphere surrounding the breathing mask and an emergency breathing valve for controlling the flow of gas from the atmosphere surrounding the breathing mask into the cavity, wherein: the exhalation valve comprises a closing body for closing an exhalation valve opening and the exhalation valve is adapted such that the exhalation valve opens when pressure in the cavity is above pressure of the atmosphere surrounding the breathing mask by a preset value; the emergency breathing valve is adapted such that the emergency breathing valve opens when pressure in the cavity is below pressure of the atmosphere surrounding the breathing mask by a preset value; the emergency breathing valve comprises a diaphragm element, which is provided with a diaphragm opening, which forms a gas connection between the cavity and the atmosphere surrounding the breathing mask; the emergency breathing valve further comprises a closing element with a closing surface, which closing element is flexible such that the closing element is deformable between an open position, in which the closing surface is located at a spaced location from the diaphragm element, so that flow of gas through the opening is allowed, and a closed position, in which the closing surface is in contact with the diaphragm element, so that the closing element closes the diaphragm opening to the atmosphere surrounding the breathing mask and flow of gas through the diaphragm opening is prevented from occurring; the closing element is a separate component of the valve arrangement; the diaphragm element is a separate component of the valve arrangement; the diaphragm element is fastened to the mask body on the side pointing away from the cavity; the closing body of the exhalation valve is held on the side pointing away from the cavity; the closing body is arranged between the diaphragm element and the mask body; the closing body is located between the closing element and the diaphragm element.

2. A breathing mask in accordance with claim 1, wherein the closing element comprises a first connection element and wherein the diaphragm element has a second connection element for meshing with the first connection element.

3. A breathing mask in accordance with claim 2, wherein: the first connection element is surrounded by the closing surface; the second connection element is arranged within the diaphragm opening and has an arm extending radially to the edge of the diaphragm opening; one of the connection elements comprises a pin extending away from the diaphragm opening; the other of the connection elements comprises a mounting opening for meshing with the pin; the diaphragm comprises one or more locking arms; and the closing body, the diaphragm element and the closing element are fastened to the mask body via the one or more locking arms.

4. A breathing mask in accordance with claim 1, wherein:
the exhalation valve has two separate exhalation valve openings adjoining the diaphragm element; and
the closing body has a one-piece design and has two flaps extending away from the diaphragm element.

5. A breathing mask in accordance with claim 1, wherein the closing body has a central opening, above which the diaphragm opening is arranged.

6. A breathing mask in accordance with claim 4, wherein the exhalation valve openings and the flaps of the closing body are arranged on opposite sides of the diaphragm element.

7. A breathing mask in accordance with claim 1, wherein:
the mask body has a main section made of a flexible material and a valve section, in which the valve assembly is provided, and which is formed from a rigid hard plastic material; and the main section surrounds the valve section.

8. A ventilation system comprising a breathing mask comprising: a mask body, which surrounds a cavity that is open towards one side and which is intended for coming into contact with a human face around the mouth and/or nose thereof, wherein the mouth and/or nose may be arranged in the cavity; a feed port for connecting a breathing gas feed device for feeding gas into the cavity; a valve arrangement comprising an exhalation valve for controlling the flow of gas from the cavity into atmosphere surrounding the breathing mask and an emergency breathing valve for controlling the flow of gas from the atmosphere surrounding the breathing mask into the cavity, wherein: the exhalation valve comprises a closing body for closing an exhalation valve opening and the exhalation valve is adapted such that the exhalation valve opens when pressure in the cavity is above pressure of the atmosphere surrounding the breathing mask by a preset value; the emergency breathing valve is adapted such that the emergency breathing valve opens when pressure in the cavity is below pressure of the atmosphere surrounding the breathing mask by a preset value; the emergency breathing valve comprises a diaphragm element, which is provided with a diaphragm opening, which forms a gas connection between the cavity and the atmosphere surrounding the breathing mask; the emergency breathing valve further comprises a closing element with a closing surface, which closing element is flexible such that the closing element is deformable between an open position, in which the closing surface is located at a spaced location from the diaphragm element, so that flow of gas through the opening is allowed, and a closed position, in which the closing surface is in contact with the diaphragm element, so that the closing element closes the diaphragm opening to the atmosphere surrounding the breathing mask and flow of gas through the diaphragm opening is prevented from occurring; the closing element is a separate component of the valve arrangement; the diaphragm element is a separate component of the valve arrangement; the diaphragm element is fastened to the mask body on the side pointing away from the cavity; the closing body of the exhalation valve is held on the side pointing away from the cavity; the closing body is arranged between the diaphragm element and the mask body; the closing body is located between the closing element and the diaphragm element; and a breathing gas feed device connected to the feed port.

9. A ventilation system in accordance with claim 8, wherein: the breathing gas feed device has a gas bag, which is provided with a connection piece, which is connected to the feed port the connection piece has an inhalation valve for controlling the flow of gas from the connection piece into the cavity; the inhalation valve is adapted such that the inhalation valve opens when the pressure in the cavity is below the pressure present in the connection piece by a preset value; the diaphragm comprises one or more locking arms; the closing body, the diaphragm element and the closing element are fastened to the mask body via the one or more locking arms.

10. A ventilation system in accordance with claim 9, wherein the connection piece has a port for a breathing gas supply line.

11. A breathing mask comprising: a mask main section; and valve section cooperating with the mask main section to form a mask body, which surrounds a cavity that is open towards one side and which is intended for coming into contact with a human face around the mouth and/or nose thereof, wherein the mouth and/or nose may be arranged in the cavity, the valve section comprising: a feed port for connecting a breathing gas feed device for feeding gas into the cavity; an exhalation valve for controlling the flow of gas from the cavity into atmosphere surrounding the breathing mask, the exhalation valve comprising a closing body for closing an exhalation valve opening and the exhalation valve is adapted such that the exhalation valve opens when pressure in the cavity is above pressure of the atmosphere surrounding the breathing mask by a preset value; and an emergency breathing valve for controlling the flow of gas from the atmosphere surrounding the breathing mask into the cavity, the emergency breathing valve being configured to open when pressure in the cavity is below pressure of the atmosphere surrounding the breathing mask by a preset value, the emergency breathing valve comprising a diaphragm element, which is provided with a diaphragm opening, which forms a gas connection between the cavity and the atmosphere surrounding the breathing mask and a closing element with a closing surface, the closing element being flexible such that the closing element is deformable between an open position, in which the closing surface is located at a spaced location from the diaphragm element, so that flow of gas through the opening is allowed, and a closed position, in which the closing surface is in contact with the diaphragm element, so that the closing element closes the diaphragm opening to the atmosphere surrounding the breathing mask and flow of gas through the diaphragm opening is prevented from occurring, the closing element being a component that is separate from other components of the valve section, the diaphragm element being separate from the other components of the valve section, the diaphragm element being fastened to the mask body on the side pointing away from the cavity, the closing body of the exhalation valve being held on the side pointing away from the cavity, the closing body being arranged between the diaphragm element and the mask body; the closing body is located between the closing element and the diaphragm element.

12. A breathing mask in accordance with claim 11, wherein: the closing element comprises a first connection element; the diaphragm element comprises a second connection element for meshing with the first connection element; the diaphragm comprises one or more locking arms;

the closing body, the diaphragm element and the closing element are fastened to the mask body via the one or more locking arms.

13. A breathing mask in accordance with claim 12, wherein:
   the first connection element is surrounded by the closing surface;
   the second connection element is arranged within the diaphragm opening and has an arm extending radially to the edge of the diaphragm opening;
   one of the connection elements comprises a pin extending away from the diaphragm opening; and
   the other of the connection elements comprises a mounting opening for meshing with the pin.

14. A breathing mask in accordance with claim 11, wherein: the exhalation valve has two separate exhalation valve openings adjoining the diaphragm element; and the closing body has a one-piece design and has two flaps extending away from the diaphragm element.

15. A breathing mask in accordance with claim 11, wherein the closing body has a central opening, above which the diaphragm opening is arranged.

16. A breathing mask in accordance with claim 14, wherein the exhalation valve openings and the flaps of the closing body are arranged on opposite sides of the diaphragm element.

17. A breathing mask in accordance with claim 11, wherein:
   the main section is made of a flexible material; and
   the valve section is formed from a rigid hard plastic material; and
   the main section surrounds the valve section.

\* \* \* \* \*